(12) United States Patent
Schuitman et al.

(10) Patent No.: US 9,233,908 B2
(45) Date of Patent: *Jan. 12, 2016

(54) CYCLOALIPHATIC DIAMINES AND METHOD OF MAKING THE SAME

(75) Inventors: Abraham D. Schuitman, Midland, MI (US); Shawn D. Feist, Midland, MI (US); Barry B. Fish, Lake Jackson, TX (US); Daniel A. Hickman, Midland, MI (US); Erich J. Molitor, Midland, MI (US); Michael L. Tulchinsky, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/383,361

(22) PCT Filed: Jul. 30, 2010

(86) PCT No.: PCT/US2010/043869
§ 371 (c)(1),
(2), (4) Date: Jan. 10, 2012

(87) PCT Pub. No.: WO2011/014747
PCT Pub. Date: Feb. 3, 2011

(65) Prior Publication Data
US 2012/0123165 A1    May 17, 2012

Related U.S. Application Data (60) Provisional application No. 61/230,319, filed on Jul. 31, 2009.

(51) Int. Cl.
*C07C 209/00* (2006.01)
*C07C 209/48* (2006.01)
*C07C 209/26* (2006.01)

(52) U.S. Cl.
CPC ............ *C07C 209/48* (2013.01); *C07C 209/26* (2013.01); *C07C 2101/14* (2013.01)

(58) Field of Classification Search
CPC ...................................................... C07C 209/26
See application file for complete search history.

(56) References Cited

U.S. PATENT DOCUMENTS 3,012,994 A    12/1961    Bell et al.
3,143,570 A    8/1964    Caldwell et al.
(Continued)

FOREIGN PATENT DOCUMENTS

EP    0011401    5/1980
EP    0394967    10/1990

OTHER PUBLICATIONS

EPO Office Action dated Dec. 17, 2014 for counterpart EPO Application No. 10739807.5, 4 pages.
(Continued)

*Primary Examiner* — Clinton Brooks (57) ABSTRACT

The instant invention provides cycloaliphatic diamines and a method of making the same. The cycloaliphatic diamines according to the instant invention comprise the reaction product of one or more cycloaliphatic cyanoaldehydes selected from the group consisting of 1,3-cyanocyclohexane carboxaldehyde, 1,4-cyanocyclohexane carboxaldehyde, mixtures thereof, and combinations thereof, hydrogen, and ammonia fed into a continuous reductive amination reactor system; wherein the one or more cycloaliphatic cyanoaldehydes, hydrogen, and ammonia are contacted with each other in the presence of one or more heterogeneous metal based catalyst systems at a temperature in the range of from 80° C. to about 160° C. and a pressure in the range of from 700 to 3500 psig; and wherein one or more cycloaliphatic diamines are formed; and wherein said one or more cycloaliphatic diamines are selected from the group consisting of 1,3-bis(aminomethyl) cyclohexane, 1,4-bis(aminomethyl)cyclohexane, combinations thereof, and mixtures thereof.

10 Claims, 7 Drawing Sheets

(56) References Cited

U.S. PATENT DOCUMENTS

| | | | |
|---|---|---|---|
| 4,101,578 | A | 7/1978 | Bock et al. |
| 4,429,157 | A * | 1/1984 | Disteldorf et al. ............ 564/446 |
| 5,041,675 | A | 8/1991 | Lukas et al. |
| 5,055,618 | A | 10/1991 | Kampmann et al. |
| 5,166,443 | A | 11/1992 | Merger |
| 5,371,293 | A | 12/1994 | Takagawa |
| 5,705,699 | A | 1/1998 | Witzel et al. |
| 5,756,845 | A | 5/1998 | Voit et al. |
| 5,789,620 | A | 8/1998 | Waldmann et al. |
| 5,986,126 | A | 11/1999 | Bunel et al. |
| 6,252,121 | B1 | 6/2001 | Argyropoulos et al. |
| 7,060,857 | B2 | 6/2006 | Funke et al. |
| 2005/0215824 | A1 | 9/2005 | Amakawa et al. |
| 2007/0005594 | A1 | 1/2007 | Pinkas et al. |
| 2008/0167499 | A1 | 7/2008 | Molitor et al. |
| 2009/0048466 | A1 | 2/2009 | Lettmann et al. |
| 2012/0116123 | A1 | 5/2012 | Santhany et al. |
| 2012/0116124 | A1 * | 5/2012 | Molitor et al. ................. 564/446 |

OTHER PUBLICATIONS

Chinese Response to Office Action dated Jul. 14, 2014; from Chinese counterpart Application No. 201080035249.6.

Japanese Response to Office Action dated Oct. 15, 2014; from Japanese counterpart Application No. 2012-523074.

Chinese Office Action dated Nov. 19, 2014; from Chinese counterpart Application No. 201080035249.6.

Instructions to Chinese Office Action dated Jan. 8, 2014; from Chinese counterpart Application No. 201080035249.6.

Foreign Associate draft response dated Jan. 7, 2014 to counterpart EPO Application No. 10739807.5 Office Action dated Oct. 18, 2013.

Response dated Jan. 29, 2014 to foreign associate EPO draft response for counterpart EPO Application No. 10739807.5 Office Action dated Oct. 18, 2013.

Response to counterpart EPO Application No. 10739807.5 Office Action dated Oct. 18, 2013 filed Feb. 7, 2014.

Gomez, "The reductive amination of aldehydes and ketones and the hydrogenation of nitriles :mechanistic aspects and selectivity control," Adv. Syn. Catal., 344 {2002} 1037•1057.

PCT/US2010/043869, International Search Report and Written Opinion.

PCT/US2010/043869, International Preliminary Report on Patentability.

Japanese Decision of Rejection dated Apr. 28, 2015 for counterpart Japanese Application No. 2012-523074, 7 pages.

EP Office Action dated Feb. 11, 2015; from corresponding EP Application No. 10739807.5.

Response to EPO Communication dated filed Mar. 31, 2015 for counterpart EPO Application No. 10739807.5.

Japanese Office Action dated Apr. 10, 2014; from counterpart Japanese Application No. 2012-523074.

Instructions to Japanese Office Action dated Oct. 9, 2014; from Japanese counterpart Application No. 2012-523074.

* cited by examiner

CYCLOALIPHATIC DIAMINES AND METHOD OF MAKING THE SAME

CROSS-REFERENCE TO RELATED APPLICATIONS

This application is a non-provisional application claiming priority from the U.S. Provisional Patent Application No. 61/230,319, filed on Jul. 31, 2009, entitled "CYCLOALIPHATIC DIAMINES AND METHOD OF MAKING THE SAME," the teachings of which are incorporated by reference herein, as if reproduced in full hereinbelow.

FIELD OF INVENTION

The instant invention relates to cycloaliphatic diamines, and a method of making the same.

BACKGROUND OF THE INVENTION

Bis(aminomethyl)cyclohexane is a diamine that has applications as a precursor to an aliphatic diisocyanate (bis(isocyanatomethyl)cyclohexane). It is useful as a chain extender in certain polyurethanes systems and can be used as an epoxy curing agent. Bis(aminomethyl)cyclohexane exists as a number of isomers, of which the 1,3- and 1,4-isomers are of primary interest. The 1,3- and 1,4-isomers can also exist in a number of diastereomeric forms, as the aminomethyl groups can each reside above or below the plane of the cyclohexane ring.

1,3- and 1,4-bis(aminomethyl)cyclohexane mixtures can be prepared via a number of synthetic routes. U.S. Pat. No. 3,143,570 describes a two-step process that requires preparation and isolation of the intermediate solid iminomethylcyclohexanecarbonitriles in water.

As another example, a route may start with butadiene and acrolein, forming 1,2,3,6-tetrahydrobenzaldehyde in a Diels-Alder reaction. This intermediate is then hydroformylated to add a second aldehyde group and reductively aminated to form the desired diamine. A mixture of isomeric forms of the diamine is obtained, as for example, described in the U.S. Pat. No. 6,252,121.

The reductive amination of hydroformylated 1,2,3,6-tetrahydrobenzaldehyde using a sponge-metal catalyst or nickel on silica gel/alumina as in U.S. Pat. No. 6,252,121, however, tends to produce diamine products in low yields. A significant portion of the starting material forms unwanted by-products and polymeric species. As a result, raw material costs may be high and purification of the crude product can be difficult and expensive. Polymeric by-products often foul the reactor and downstream purification unit operations.

It is sometimes possible to suppress by-product formation in reductive amination reactions by "protecting" (or "blocking") the aldehyde groups with an alkyl amine as, for example, described in the U.S. Pat. Nos. 5,041,675 and 5,055,618. The blocked groups are more resistant to polymerization and other unwanted side reactions. However, this approach requires the use of additional raw materials and introduces additional chemical species into the reaction, which must later be removed from the crude product and recycled. Process yields are still far short of those that are needed to have a highly economical process.

Additionally, the production of 1,3- and 1,4-bis(aminomethyl)cyclohexane via a dialdehyde intermediate may be difficult due to catalyst deactivation that leads to rapidly declining yields. Although more stable catalysts have been identified, these catalysts provide lower yields from the very beginning of operation. In addition, the dialdehyde intermediate route requires a reliable and sufficient supply of acrolein.

In order to overcome these catalyst performance issues and avoid potential future acrolein supply issues, the instant invention provides reductive amination of 1,3- and 1,4-cyanocyclohexane carboxaldehyde (CCA). This intermediate is based on an acrylonitrile feedstock, which is more accessible than acrolein. Simultaneous reduction of the nitrile group and reductive amination of the aldehyde functionality requires a specialized catalyst. Traditional nitrile reduction conditions and catalysts are more aggressive than aldehyde reductive amination conditions and catalysts. Thus, catalysts and conditions that are effective for complete reduction of the nitrile group may also have a tendency to reduce the aldehyde to the corresponding alcohol, resulting in a yield loss. On the other hand, catalysts and conditions that are typically chosen for reductive amination of an aldehyde are typically ineffective in providing complete reduction of the nitrile group, resulting in yield losses to the intermediate aminonitriles. Additionally, the relatively short lifetime of current catalysts introduces other challenges. Catalysts providing good yields to the diamine product (1,3- and 1,4-bis(aminomethyl)cyclohexanes) consistently lose their activity for the nitrile hydrogenation step within less than 250 hours of time on stream. Economically viable catalysts for this process require a much higher number of hours of lifetime, or, equivalently, pounds of 1,3- and 1,4-bis(aminomethyl)cyclohexanes produced per pound of catalyst.

Accordingly, it would be desirable to provide a method by which cycloaliphatic bis(aminomethyl) compounds can be prepared economically and in high yield.

SUMMARY OF THE INVENTION

The instant invention provides cycloaliphatic diamines and a method of making the same.

In one embodiment, the instant invention provides cycloaliphatic diamines comprising the reaction product of one or more cycloaliphatic cyanoaldehydes selected from the group consisting of 1,3-cyanocyclohexane carboxaldehyde, 1,4-cyanocyclohexane carboxaldehyde, mixtures thereof, and combinations thereof, hydrogen, and ammonia fed into a reductive amination reactor system; wherein the one or more cycloaliphatic cyanoaldehydes, hydrogen, and ammonia are contacted with each other in the presence of one or more heterogeneous metal based catalyst systems at a temperature in the range of from 80° C. to about 160° C. and a pressure in the range of from 700 to 3500 psig; and wherein one or more cycloaliphatic diamines are formed; and wherein said one or more cycloaliphatic diamines are selected from the group consisting of 1,3-bis(aminomethyl)cyclohexane, 1,4-bis(aminomethyl)cyclohexane, combinations thereof, and mixtures thereof.

In an alternative embodiment, the instant invention further provides a process for producing cycloaliphatic diamines comprising the steps of (1) feeding one or more cycloaliphatic cyanoaldehydes selected from the group consisting of 1,3-cyanocyclohexane carboxaldehyde, 1,4-cyanocyclohexane carboxaldehyde, mixtures thereof, and combinations thereof, hydrogen, and ammonia into a reductive amination reactor system; (2) contacting the one or more cycloaliphatic cyanoaldehydes, hydrogen, and ammonia with each other in the presence of one or more heterogeneous metal based catalyst systems at a temperature in the range of from 80° C. to about 160° C. and a pressure in the range of from 700 to 3500 psig; and (3) thereby forming one or more cycloaliphatic diamines, wherein said one or more cycloaliphatic diamines are diamines selected from the group consisting of 1,3-bis (aminomethyl)cyclohexane, 1,4-bis(aminomethyl)cyclohexane, combinations thereof, and mixtures thereof.

In another alternative embodiment, the instant invention further provides a method of improving the production yield of cycloaliphatic diamines comprising the steps of (1) contacting one or more cycloaliphatic cyanoaldehydes selected from the group consisting of 1,3-cyanocyclohexane carboxaldehyde, 1,4-cyanocyclohexane carboxaldehyde, mixtures thereof, and combinations thereof, hydrogen, and ammonia with each other in the presence of one or more heterogeneous metal based catalyst systems at a temperature in the range of from 80° C. to about 160° C. and a pressure in the range of from 1400 to 2500 psig; (2) thereby improving the product yield of one or more cycloaliphatic diamines, wherein said one or more cycloaliphatic diamines are diamines selected from the group consisting of 1,3-bis(aminomethyl)cyclohexane, 1,4-bis(aminomethyl)cyclohexane, combinations thereof, and mixtures thereof.

In an alternative embodiment, the instant invention provides cycloaliphatic diamines and a method of making the same, and a method of improving the production yield of cycloaliphatic diamines, in accordance with any of the preceding embodiments, except that one or more cycloaliphatic cyanoaldehydes are contacted with ammonia first and then the mixture is contacted with hydrogen in the presence of one or more heterogeneous metal based catalyst systems.

In an alternative embodiment, the instant invention provides cycloaliphatic diamines and a method of making the same, and a method of improving the production yield of cycloaliphatic diamines, in accordance with any of the preceding embodiments, except that the reactor system comprises one or more continuous reactors comprising fixed bed reactors, slurry reactors, or combinations thereof.

In an alternative embodiment, the instant invention provides cycloaliphatic diamines and a method of making the same, and a method of improving the production yield of cycloaliphatic diamines, in accordance with any of the preceding embodiments, except that fixed bed reactors comprise trickle bed reactors, packed bubble column reactors, or countercurrent flow reactors.

In an alternative embodiment, the instant invention provides cycloaliphatic diamines and a method of making the same, and a method of improving the production yield of cycloaliphatic diamines, in accordance with any of the preceding embodiments, except that slurry reactors comprise stirred tank slurry reactors, slurry bubble column reactors, circulating fluidized bed reactors, or ejector nozzle loop reactors.

In an alternative embodiment, the instant invention provides cycloaliphatic diamines and a method of making the same, and a method of improving the production yield of cycloaliphatic diamines, in accordance with any of the preceding embodiments, except that the semi-batch or batch reactors comprise fixed bed reactors or slurry reactors, or combinations thereof.

In an alternative embodiment, the instant invention provides cycloaliphatic diamines and a method of making the same, and a method of improving the production yield of cycloaliphatic diamines, in accordance with any of the preceding embodiments, except that the fixed bed reactors comprise trickle bed reactors, packed bubble column reactors, or countercurrent flow reactors.

In an alternative embodiment, the instant invention provides cycloaliphatic diamines and a method of making the same, and a method of improving the production yield of cycloaliphatic diamines, in accordance with any of the preceding embodiments, except that the slurry reactors comprise stirred tank slurry reactors, slurry bubble column reactors, circulating fluidized bed reactors, or ejector nozzle loop reactors.

In an alternative embodiment, the instant invention provides cycloaliphatic diamines and a method of making the same, and a method of improving the production yield of cycloaliphatic diamines, in accordance with any of the preceding embodiments, except that the one or more heterogeneous metal based catalyst systems are contacted with hydrogen at a temperature in the range of from 200° C. to 500° C. prior to contacting with the complete reaction mixture.

In an alternative embodiment, the instant invention provides cycloaliphatic diamines and a method of making the same, and a method of improving the production yield of cycloaliphatic diamines, in accordance with any of the preceding embodiments, except that one or more heterogeneous metal based catalyst systems are contacted with a mixture that comprises ammonia, solvents, hydrogen, mixtures thereof, and combinations thereof, at a temperature in the range of from 0° C. to 80° C. prior to contacting with the complete reaction mixture.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

DETAILED DESCRIPTION OF THE INVENTION

The instant invention provides cycloaliphatic diamines and a method of making the same. The cycloaliphatic diamines according to the instant invention comprise the reaction product of one or more cycloaliphatic cyanoaldehydes selected from the group consisting of 3-cyanocyclohexane-1-carboxaldehyde, 4-cyanocyclohexane-1-carboxaldehyde, mixtures thereof, and combinations thereof, hydrogen, and ammonia fed into a reductive amination reactor system, e.g. one or more continuous reactors, one or more batch reactors, one or more semi-batch reactors, or combinations thereof; wherein the one or more cycloaliphatic cyanoaldehydes, hydrogen, and ammonia are contacted with each other in the presence of one or more heterogeneous metal based catalyst systems at a temperature in the range of from 80° C. to about 160° C. and a pressure in the range of from 700 to 3500 psig; and wherein one or more cycloaliphatic diamines are formed; and wherein said one or more cycloaliphatic diamines are selected from the group consisting of 1,3-bis(aminomethyl)cyclohexane, 1,4-bis(aminomethyl)cyclohexane, combinations thereof, and mixtures thereof.

The one or more cycloaliphatic cyanoaldehydes may be selected from the group consisting of 3-cyanocyclohexane carboxaldehyde, 4-cyanocyclohexane carboxaldehyde, mixtures thereof, and combinations thereof.

3-cyanocyclohexane carboxaldehyde, CAS No. 50738-61-9, may have the following structure and formula:

$C_8H_{11}NO$
Mol. Wt.: 137.179

4-cyanocyclohexane carboxaldehyde, CAS No. 18214-33-0, may have the following structure and formula:

$C_8H_{11}NO$
Mol. Wt.: 137.179

The reaction between one or more cycloaliphatic cyanoaldehydes, hydrogen, and ammonia may take place in the presence of one or more heterogeneous metal based catalyst systems at a temperature in the range of from 60° C. to 200° C., for example from 80° C. to about 160° C. or from 90° C. to about 130° C., and a pressure in the range of from 500 to 5000 psig, for example from 700 to 3500 psig or from 1400 to 2500 psig. Such one or more heterogeneous metal based catalyst systems may comprise a metal selected from the group consisting of Co, Ni, Ru, Fe, Cu, Re, Pd, oxides thereof, mixtures thereof, and combinations thereof. Such one or more heterogeneous metal based catalyst systems may comprise a bulk metal catalyst system, sponge-metal catalyst system, supported metal catalyst system, mixtures thereof, or combinations thereof. Such one or more heterogeneous metal based catalyst systems may comprise a bulk Co based catalyst system. In a continuous process, the catalyst lifetime facilitates a weight ratio of the one or more cycloaliphatic diamines to one or more heterogeneous metal based catalyst systems that is greater than 300; for example, greater than 500; or in the alternative greater than 900; or in the alternative greater than 1000. The one or more heterogeneous metal based catalyst systems may further comprise a sponge-metal catalyst. The one or more heterogeneous metal based catalyst systems may further comprise one or more promoters or one or more binding agents or one or more catalyst supports. Such one or more promoters may be selected from the group consisting of alkali metals, and alkaline earth metals. Such one or more binding agents may comprise silicon oxide, aluminum oxide, titanium oxide, zirconium oxide, mixtures thereof, or combinations thereof. Such one or more catalyst supports may comprise silicon oxide, aluminum oxide, titanium oxide, zirconium oxide, mixtures thereof, or combinations thereof. Such one or more heterogeneous metal based catalyst systems are commercially available as Raney Cobalt Catalyst from Grace Davison Catalyst Company, Co-0179T cobalt catalyst from BASF, Co-138E cobalt catalyst from BASF, and G-103 cobalt catalyst from Süd-Chemie.

In a continuous process, the cost of the catalyst depends on its lifetime, which is equivalent to the weight of product produced per pound of catalyst required. An adequately long lifetime is required for an economically viable continuous process. The one or more heterogeneous metal based catalyst systems may be present in an amount necessary to catalyze the reaction between the one or more cycloaliphatic cyanoaldehydes, hydrogen, and ammonia. For example, the catalyst lifetime facilitates a weight ratio of the cycloaliphatic diamines to the one or more heterogeneous metal based catalyst systems to be greater than 300, for example, greater than 500; or in the alternative, greater than 900; or in the alternative, greater than 1000. In one embodiment, the one or more heterogeneous metal based catalyst systems may, for example, comprise a continuous fixed bed catalyst system.

The one or more heterogeneous metal based catalyst systems may be present in an amount necessary to catalyze the reaction between the one or more cycloaliphatic cyanoaldehydes, hydrogen, and ammonia. The space velocity, which is defined as mass of one or more cycloaliphatic cyanoaldehydes mixture per mass of catalyst per hour, is in the range of from 0.1 to 10.0 per hour; for example, from 0.1 to 5.0 per hour; or in the alternative, from 0.1 to 3.0 per hour; or in the alternative, from 0.1 to 2.0 per hour; or in the alternative, from 0.1 to 1.0 per hour; or in the alternative, from 0.3 to 0.8 per hour.

Ammonia is present in excess amount relative to the one or more cycloaliphatic cyanoaldehydes. Ammonia may, for example, be present in a range of 2 to 50 moles per mole of one or more cycloaliphatic cyanoaldehydes; or in the alternative, in a range of 5 to 40 moles per mole of one or more cycloaliphatic cyanoaldehydes; or in the alternative, in a range of 8 to 30 moles per mole of one or more cycloaliphatic cyanoaldehydes. Hydrogen may, for example, be present in a range of 3 to 30 moles per mole of one or more cycloaliphatic cyanoaldehydes; or in the alternative, in a range of 3 to 10 moles per mole of one or more cycloaliphatic cyanoaldehydes; or in the alternative, in a range of 3 to 6 moles per mole of one or more cycloaliphatic cyanoaldehydes.

The reaction between one or more cycloaliphatic cyanoaldehydes, hydrogen, and ammonia may optionally take place in the presence of one or more solvents. Such solvents include, but are not limited to, water; 2-propanol(isopropylalcohol), CAS No. 67-63-0; methanol, CAS No. 67-56-1; t-butanol, CAS No. 75-65-0; and tetrahydrofuran (THF), CAS No. 109-99-9. The feed into the reactor may comprise 0 to 90 percent by weight of one or more solvents, based on the combined weight of one or more cycloaliphatic cyanoaldehydes and the one or more solvents; or in the alternative, 0 to 30 percent by weight of one or more solvents, based on the combined weight of one or more cycloaliphatic cyanoaldehydes and the one or more solvents; or in the alternative, 0 to 10 percent by weight of one or more solvents, based on the combined weight of one or more cycloaliphatic cyanoaldehydes and the one or more solvents.

The reaction between one or more cycloaliphatic cyanoaldehydes, hydrogen, and ammonia may take place in a continuous reductive amination reactor system; or in the alternative, it may take place in a batch reactor system; or in the alternative, it may take place in a semi-batch reactor system. Such reactor systems are generally known to a person of ordinary skill in the art. The continuous reductive amination reactor system, the semi-batch reductive amination reactor system, or the batch reductive amination reactor system may comprise one or more reactors in series, in parallel, or combinations thereof.

The one or more cycloaliphatic diamines produced according to the instant invention may be selected from the group consisting of 1,3-bis(aminomethyl)cyclohexane, 1,4-bis(aminomethyl)cyclohexane, combinations thereof, and mixtures thereof.

1,3-bis(aminomethyl)cyclohexane, CAS No. 2579-20-6, may have the following structure or formula:

$C_8H_{18}N_2$
Mol. Wt.: 142.242

1,4-bis(aminomethyl)cyclohexane, CAS No. 2549-93-1, may have the following structure or formula:

$C_8H_{18}N_2$
Mol. Wt.: 142.242

Additional byproducts may include 3-(aminomethyl)-cyclohexanecarbonitrile, CAS No. 23083-50-3; 4-(aminomethyl)-cyclohexanecarbonitrile, CAS No. 54898-73-6; 3-azabicyclo[3.3.1]nonane, CAS No. 280-70-6; 3-azabicyclo[3.3.1]non-2-ene, CAS No. 7129-32-0; 7-amino-bicyclo[2.2.1]heptane-1-methanamine; 3-(aminomethyl)-cyclohexanemethanol, CAS No. 925921-54-6; 4-(aminomethyl)-cyclohexanemethanol, CAS No. 1074-62-0.

The process for producing cycloaliphatic diamines according to the instant invention comprises the steps of (1) feeding one or more cycloaliphatic cyanoaldehydes selected from the group consisting of 1,3-cyanocyclohexane carboxaldehyde, 1,4-cyanocyclohexane carboxaldehyde, mixtures thereof, and combinations thereof, hydrogen, and ammonia into a reductive amination reactor system; (2) contacting the one or more cycloaliphatic cyanoaldehydes, hydrogen, and ammonia with each other in the presence of one or more heterogeneous metal based catalyst systems at a temperature in the range of from 80° C. to about 160° C. and a pressure in the range of from 700 to 3500 psig; and (3) thereby forming one or more cycloaliphatic diamines, wherein said one or more cycloaliphatic diamines are diamines selected from the group consisting of 1,3-bis(aminomethyl)cyclohexane, 1,4-bis(aminomethyl)cyclohexane, combinations thereof, and mixtures thereof.

In a process for producing cycloaliphatic diamines according to the instant invention, one or more cycloaliphatic cyanoaldehydes, hydrogen, ammonia, and optionally one or more solvents are introduced into a reductive amination reactor system and reacted with each other in the presence of one or more heterogeneous metal based catalyst systems at a temperature in the range of from 80° C. to about 160° C. and a pressure in the range of from 700 to 3500 psig to yield one or more cycloaliphatic diamines.

In one embodiment, one or more cycloaliphatic cyanoaldehydes are contacted with ammonia first and then the product mixture including the product of the reaction of one or more cycloaliphatic cyanoaldehydes with ammonia is contacted with hydrogen in the presence of one or more heterogeneous metal based catalyst systems.

A product mixture including one or more aliphatic diamines, optionally a portion of the product of the reaction of one or more cycloaliphatic cyanoaldehydes with ammonia, optionally a portion of the ammonia, optionally a portion of the hydrogen, optionally a portion of one or more by-products, optionally a portion of the water, and optionally a portion of the one or more solvents is formed in the one or more reactor systems, as described hereinabove. The product mixture is then removed from the one or more reactor systems and transferred to one or more distillation columns arranged in sequential order. After the product mixture is transferred to one or more distillation columns arranged in sequential order, at least a portion of the ammonia, a portion of the hydrogen, or a mixture thereof is removed from the product mixture via one or more distillation steps. Subsequently, at least a portion of the one or more solvents, if optionally present, and/or water is removed via one or more distillation steps. Subsequently, at least a portion of the product of the reaction of one or more cycloaliphatic cyanoaldehydes with ammonia or one or more by-products is removed via one or more distillation steps, thus separating the one or more aliphatic diamines from the product mixture and converting the one or more cyanoaldehydes to one or more aliphatic diamines. The distillation process is further described in the U.S. provisional patent application with Ser. No. 61/230,300 incorporated herein by reference in its entirety.

The method of improving the production yield of cycloaliphatic diamines according to the instant invention comprises the steps of (1) contacting one or more cycloaliphatic cyanoaldehydes selected from the group consisting of 1,3-cyanocyclohexane carboxaldehyde, 1,4-cyanocyclohexane carboxaldehyde, mixtures thereof, and combinations thereof, hydrogen, and ammonia with each other in the presence of one or more heterogeneous metal based catalyst systems at a temperature in the range of from 80° C. to about 160° C. and a pressure in the range of from 1400 to 2500 psig; (2) thereby improving the product yield of one or more cycloaliphatic diamines, wherein said one or more cycloaliphatic diamines are diamines selected from the group consisting of 1,3-bis(aminomethyl)cyclohexane, 1,4-bis(aminomethyl)cyclohexane, combinations thereof, and mixtures thereof.

The one or more cycloaliphatic diamines produced according to the instant invention may be used as a precursor to an aliphatic diisocyanate (bis(isocyanatomethyl)cyclohexane), as a chain extender in certain polyurethanes systems, or as an epoxy curing agent.

EXAMPLES

The following examples illustrate the present invention but are not intended to limit the scope of the invention.

Inventive Examples A-G were prepared in a batch reactor according to following procedures.

Inventive Example A

A mixture of 3- and 4-cyanocyclohexane-1-carboxaldehydes (1.001 g; 7.30 millimoles) and diglyme (0.4004 g, internal standard) was charged to an 80 ml Parr reactor, a high pressure reactor, containing Raney Co 2724 catalyst modified with Ni—Cr (0.2 g) provided by Grace Davison, ammonia (in liquid form) (6.82 g; 401 mmol), and methanol (as a solvent)

(25 ml). The reactor was heated to 120° C. within 10-15 minutes. Then hydrogen was charged to approximately 1,000 psi and the reaction mixture was stirred at 120° C. for 3 hrs. According to gas chromatography analysis of the reactor contents, 1,3- and 1,4-bis(aminomethyl)cyclohexanes were obtained in 96 percent yield, and only about 2 percent of 3-azabicyclo[3.3.1]-nonane (bicyclic byproduct) was detected in the reaction mixture.

Inventive Example B

The procedure described in Inventive Example A was repeated except that 1.68 g (99 mmol) of ammonia was used in place of 6.82 g (401 mmol) of ammonia. The yields of 1,3- and 1,4-bis(aminomethyl)cyclohexanes and 3-azabicyclo [3.3.1]nonane were 91 percent and 6 percent, respectively.

Inventive Example C

The procedure described in Inventive Example A was repeated except that n-butanol was used as the solvent instead of methanol. The yields of 1,3- and 1,4-bis(aminomethyl) cyclohexanes and 3-azabicyclo[3.3.1]nonane were 92 percent and 4 percent, respectively.

Inventive Example D

The procedure described in Inventive Example A was repeated except that Grace Davison Raney Ni 2400 catalyst modified with Cr was used instead of the Raney Co 2724 catalyst. The yields of 1,3- and 1,4-bis(aminomethyl)cyclohexanes and 3-azabicyclo[3.3.1]nonane were 96 percent and 4 percent, respectively.

Inventive Example E

The procedure described in Inventive Example A was repeated except that Grace Davison Raney Ni 3110 catalyst modified with Mo (molybdenum) was used instead of Raney Co 2724 catalyst. The yields of 1,3- and 1,4-bis(aminomethyl)cyclohexanes and 3-azabicyclo[3.3.1]nonane were 92 percent and 8 percent, respectively.

Inventive Example F

The procedure described in Inventive Example A was repeated except that Aldrich 208779 nickel on silica/alumina catalyst was used instead of Raney cobalt catalyst. The yields of 1,3- and 1,4-bis(aminomethyl)cyclohexanes and 3-azabicyclo[3.3.1]nonane were 90 percent and 10 percent, respectively.

Inventive Example G

Twenty-eight catalysts were screened in a 450 mL Parr reactor. Granular and formed catalysts were first ground to provide for a direct comparison with other powdered materials. All catalysts were first treated with hydrogen at 30 psig and 180° C. for one hour. Then, the reactor was evacuated and a methanol/ammonia mixture was charged to the reactor at room temperature. The reactor was then heated to the reaction temperature, approximately 130° C., with agitation, and the reactant cyanoaldehyde was injected into the reactor. The reactor was then pressurized to 1000 psig with hydrogen. Hydrogen was supplied as needed to maintain 1000 psig until the hydrogen uptake ceased. The reactor was then cooled and sampled. The Grace Davison Raney Co 2786 gave 10.7 g product (1,3- and 1,4-bis(aminomethyl)cyclohexanes)/g bicyclic byproduct (3-azabicyclo[3.3.1]nonane), with an integrated (time-averaged) rate of 6.19 g product/g catalyst-hr.

Inventive Examples 1-5 were prepared in a continuous fixed bed reactor according to the following procedures.

Inventive Example 1

Figure 1:
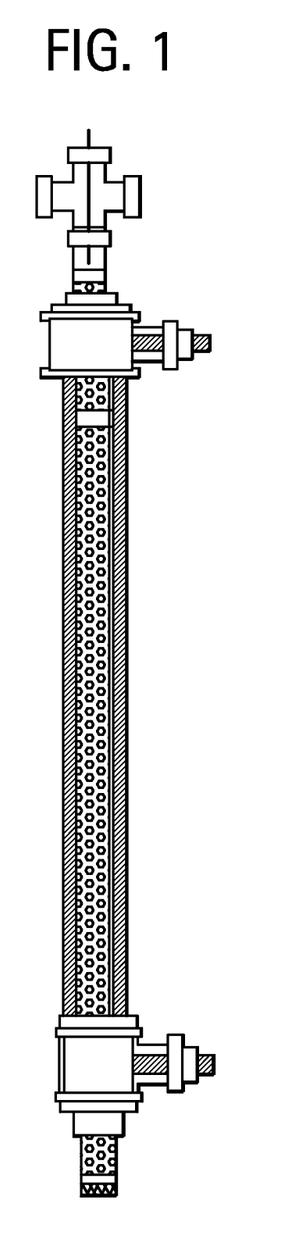
FIG. 1 illustrates an exemplary tube reactor.
Figure 2:
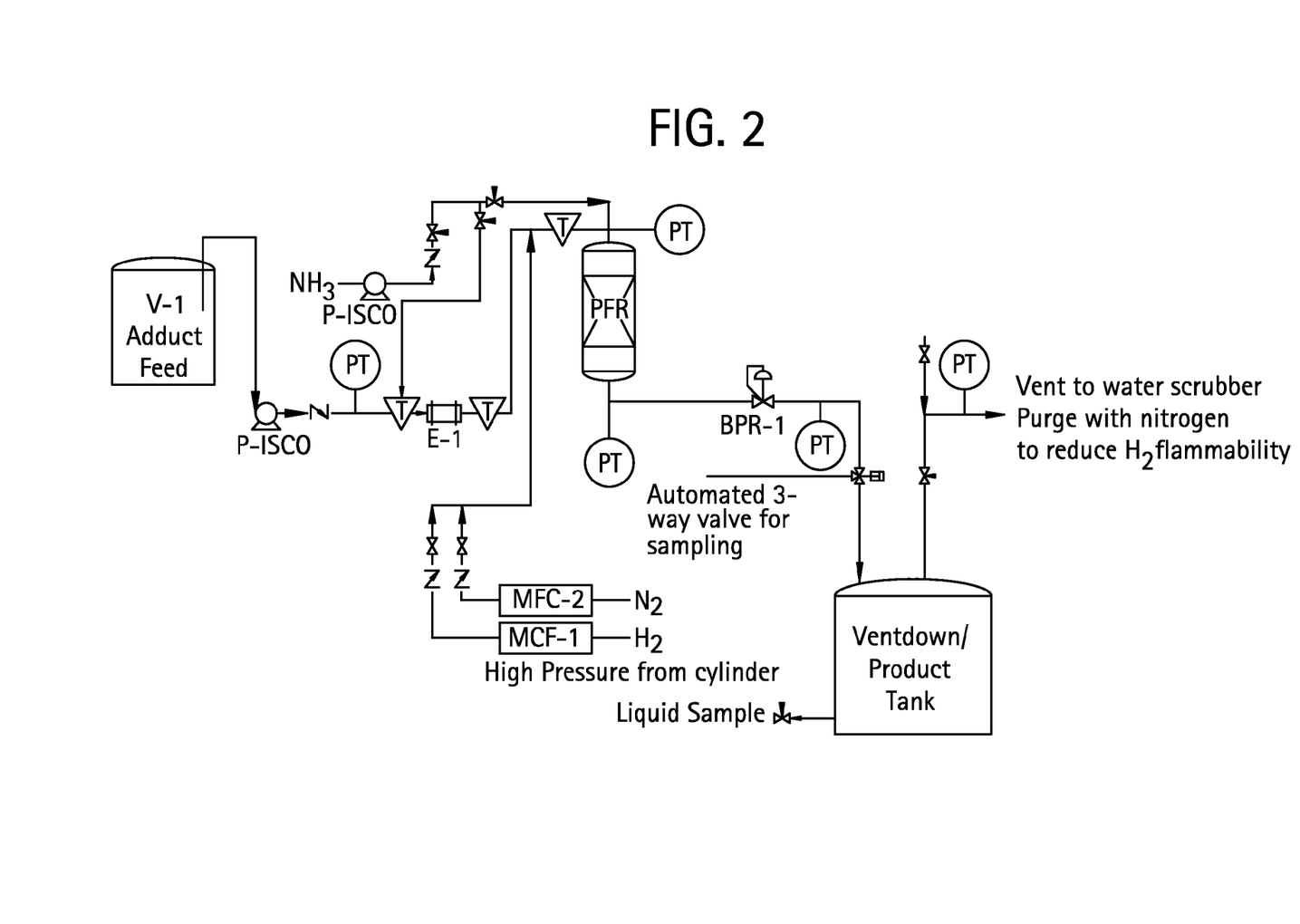
FIG. 2 is a schematic illustrating an exemplary process flow diagram for a laboratory system for testing catalyst systems.
Figure 3:
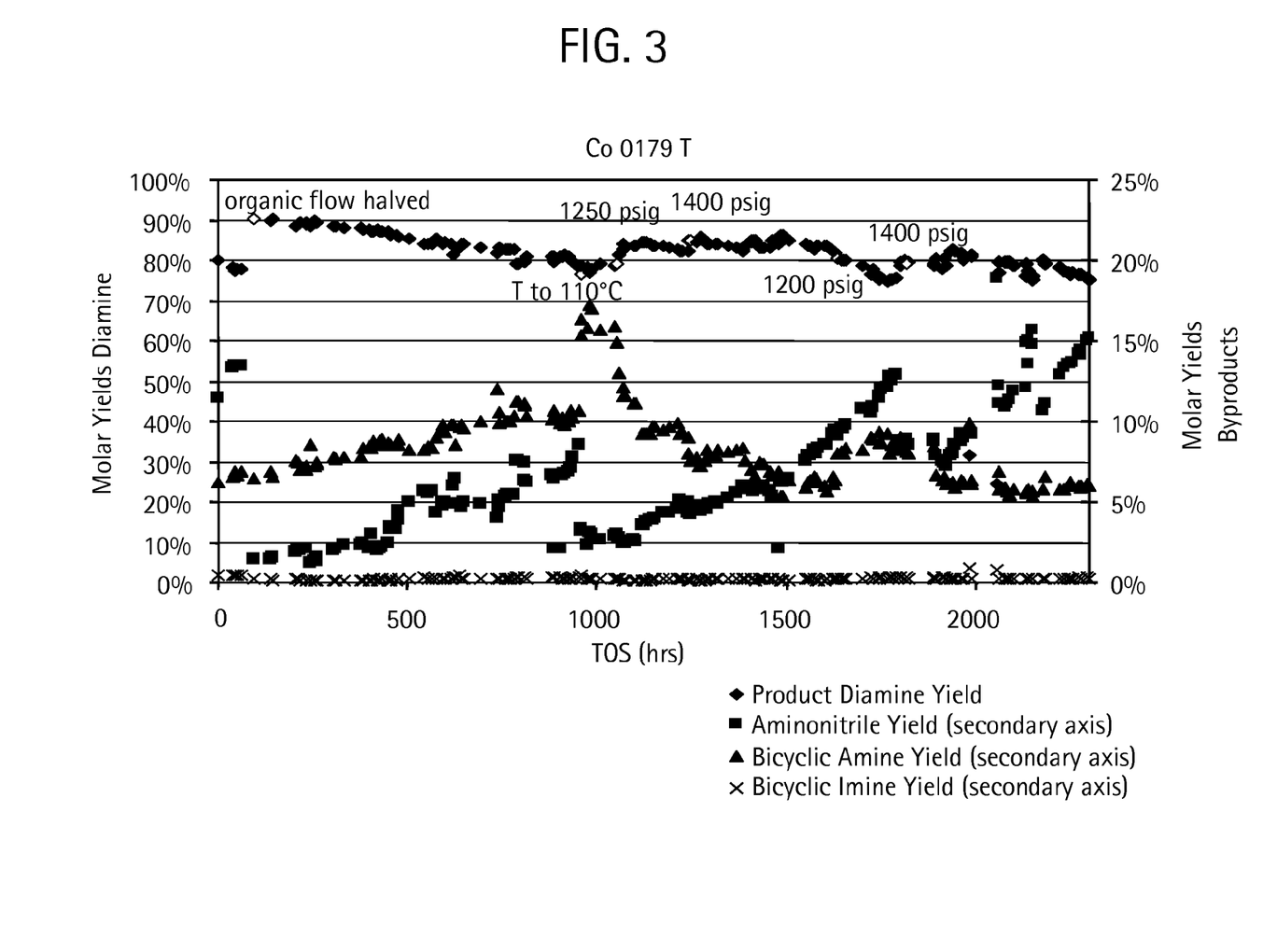
FIG. 3 is a graph illustrating the relationship between time on stream and molar yields of Inventive Example 1.

A reactor feed mixture was prepared by distilling crude cyanoaldehyde comprising approximately 85 to 90 percent by weight of cyanoaldehyde, combining the overheads with a small amount (few hundred ppm) of Isonox 132, an antioxidant. The distilled cyanoaldehyde was diluted to 25 weight percent in tetrahydrofuran (THF). The mixture was passed through a bed of sodium carbonate (pretreatment of feed) and sparged with nitrogen. A reactor tube was loaded with 5.5 g Co-0179T catalyst provided by BASF, diluted with 100 grit (150 μm) SiC (silicon carbide) fines. A schematic of the designed reactor can be seen in FIG. 1; FIG. 2 illustrates the flow diagram for the reactor system. The catalyst was treated with flowing hydrogen at 200° C. overnight prior to startup. After reducing the reactor temperature to <80° C. under continued hydrogen flow, an excess flow of ammonia (at least 3-5 times desired set point, as described hereinbelow) was initiated, followed by the same proportional excess flow of the organic mixture, i.e. cyanoaldehydes and THF. The temperature and pressure were then set to the desired set points of 100° C. and 1000 psig. After at least one hour, the ammonia and organic feed rates were decreased to the desired set points of 0.22 mL/min each, a weight hourly space velocity (based on combined organic and ammonia mass feed rates) of 5 $hr^{-1}$ with a hydrogen to cyanoaldehyde molar ratio of 10. Samples were periodically collected from the reactor and analyzed by gas chromatography. Samples collected between 0 and 64 hours on stream showed 77-80 percent molar yield of diamines (1,3- and 1,4-bis(aminomethyl)cyclohexanes), with 11-14 percent molar yield of aminonitrile and 6-7 percent molar yield of bicyclic amine(3-azabicyclo[3.3.1]nonane), with no significant change in the product distribution over this period, indicating stable catalyst performance. Then, the feed rates were halved, decreasing the WHSV (weight hourly space velocity) to 2.5 $hr^{-1}$. Samples collected between 95 and 232 hours on stream showed 88-90 percent molar yield of diamines (1,3- and 1,4-bis(aminomethyl)cyclohexanes), with 1.4-2.1 percent molar yield of aminonitrile and 6-8 percent molar yield of bicyclic amine(3-azabicyclo[3.3.1]nonane), with no significant change in the product distribution over this period, indicating stable catalyst performance. A small degradation in catalyst performance can be seen in FIG. 3 through 950 hours of run time (aminonitrile yield, bicyclic amine yield, and bicyclic imine all on the secondary axis), but this decline is relatively quite small. Temperature was increased to 110° C. at 950 hours. The pressure was increased from 1000 psig to 1250 psig at 1075 hours time on stream. A significant gain in selectivity was realized from the increase in pressure as the bicyclic amine was reduced from 15% to 9%, and the product diamine yield was increased from 79% to 84% (seen in FIG. 3). A similar gain was also realized as the pressure was further increased from 1250 psig to 1400 psig (bicyclic amine yield fell from 9% to 7% with a jump in diamine yield from 82% to 85%). Productivity for this run remained consistently around $5.0 \times 10^{-7}$ moles diamine/g-catalyst/s. Table 1 displays the cobalt leaching numbers in ppm. Higher pressures yielded lower cobalt in the diamine product. These metal concentration numbers were generated by inductively coupled plasma mass spectroscopy (ICP-MS).

Inventive Example 2

Figure 4:
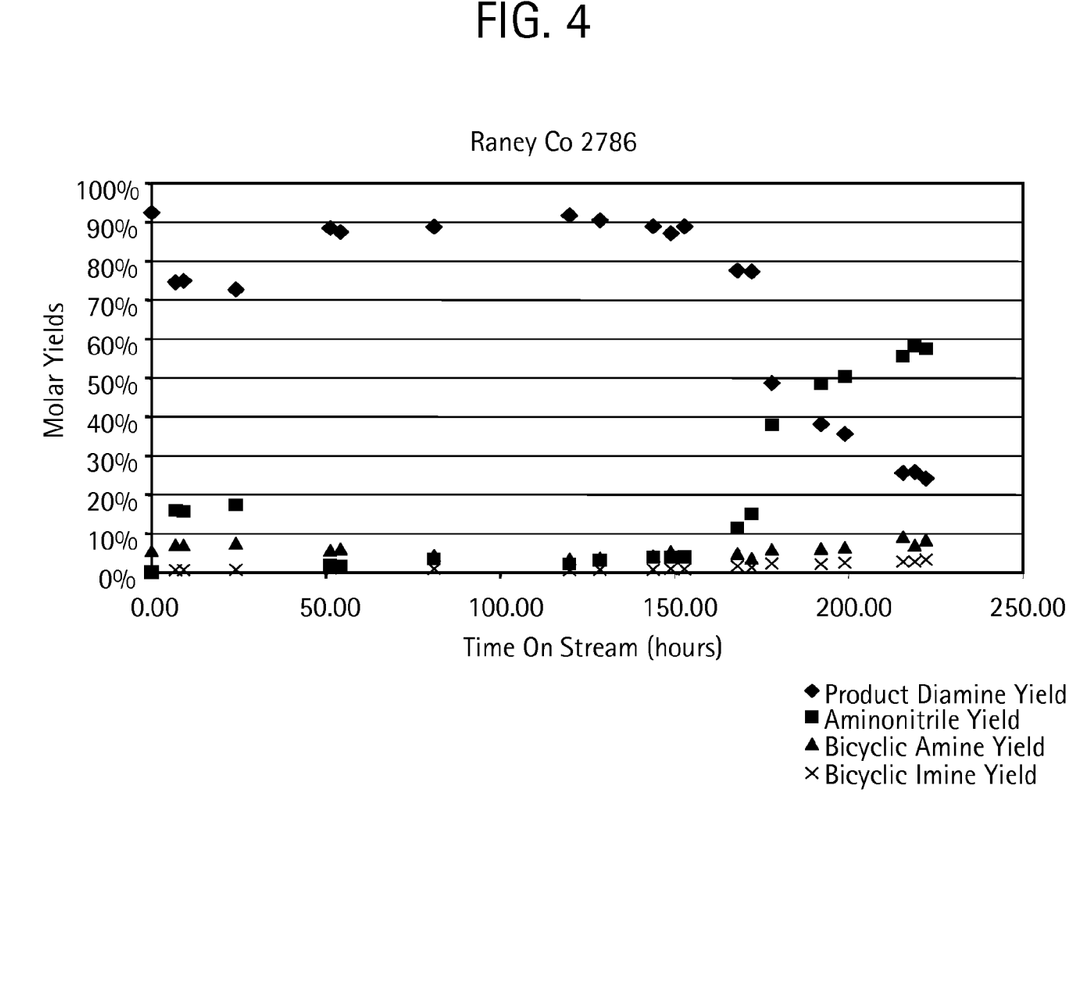
FIG. 4 is a graph illustrating the relationship between time on stream and molar yields of Inventive Example 2.

A reactor tube was loaded with 20.0 g (water wet) Grace Davison Raney Co 2786, 8×12 mesh, diluted with 100 grit (150 μm) SiC fines. The organic feed was the same as the feed description in Inventive Example 1. The temperature and pressure were then set to the desired set points of 107° C. and 1100 psig. The ammonia and organic feed rates were initially set to 0.11 and 0.22 mL/min; then the organic was halved to 0.11 mL/min at 25 hours, respectively. Samples were periodically collected from the reactor and analyzed by gas chromatography. Samples collected between 50 and 150 hours on stream showed 87-91 percent molar yield of diamines (1,3- and 1,4-bis(aminomethyl)cyclohexanes), with 0-4 percent molar yield of aminonitrile and 4-6 percent molar yield of bicyclic amine(3-azabicyclo[3.3.1]nonane). Samples collected after 150 hours on stream with the same feed and reactor conditions showed a continuing decline in diamine yield, with an increase in the aminonitrile and bicyclic amine (3-azabicyclo[3.3.1]nonane) yields, and with the diamine yield falling to 50 percent by 175 hours on stream, as shown in FIG. 4.

Inventive Example 3

Figure 5:
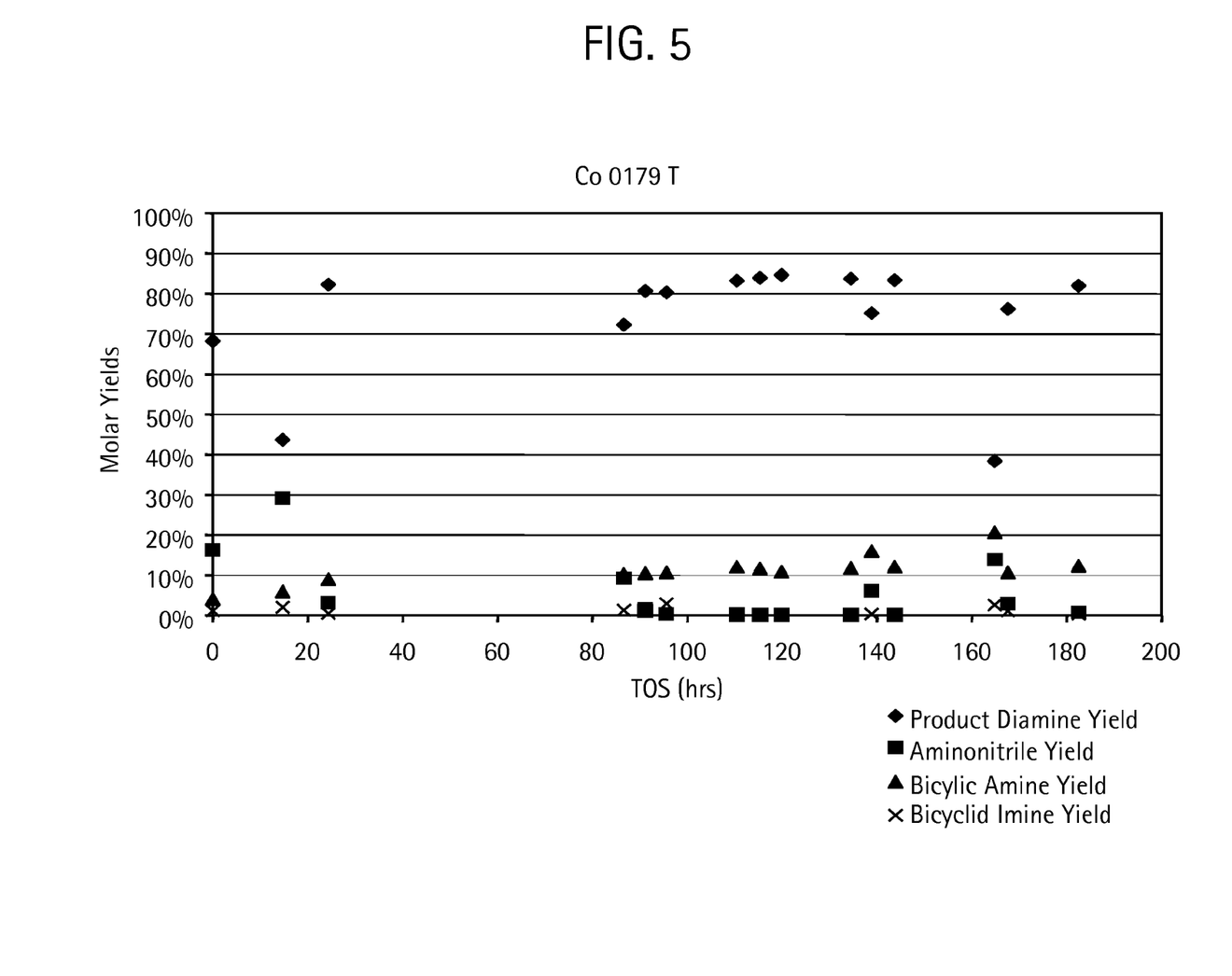
FIG. 5 is a graph illustrating the relationship between time on stream and molar yields of Inventive Example 3.

A reactor tube was loaded with 6.27 g Co-0179T catalyst provided by BASF, diluted with 100 grit (150 μm) SiC fines. The organic feed for this reactor was crude cycloaliphatic cyanoaldehydes (CCA) comprising approximately 85 to 90 percent by weight of cyanoaldehyde fed neat to the reactor. The catalyst was treated with flowing hydrogen at 200° C. overnight prior to startup. After reducing the reactor temperature to <80° C. under continued hydrogen flow, an excess flow of ammonia (at least 3-5 times desired set point) was initiated. The temperature and pressure were then set to the desired set points of 100° C. and 1000 psig. After at least one hour, the ammonia was decreased to the desired set point of 0.44 mL/min, and the organic was started at 0.11 mL/min. The ammonia and organic feed rates were reduced to 0.13 and 0.03 mL/min, respectively, after 30 hours with a hydrogen to CCA molar ratio of 7. Samples were periodically collected from the reactor and analyzed by gas chromatography. Samples collected between 90 and 185 hours on stream showed 80-85 percent molar yield of diamines (1,3- and 1,4-bis(aminomethyl)cyclohexanes), with 0-1 percent molar yield of aminonitrile and 10-12 percent molar yield of bicyclic amine(3-azabicyclo[3.3.1]nonane). Catalyst performance is shown in FIG. 5.

Inventive Example 4

Figure 6:
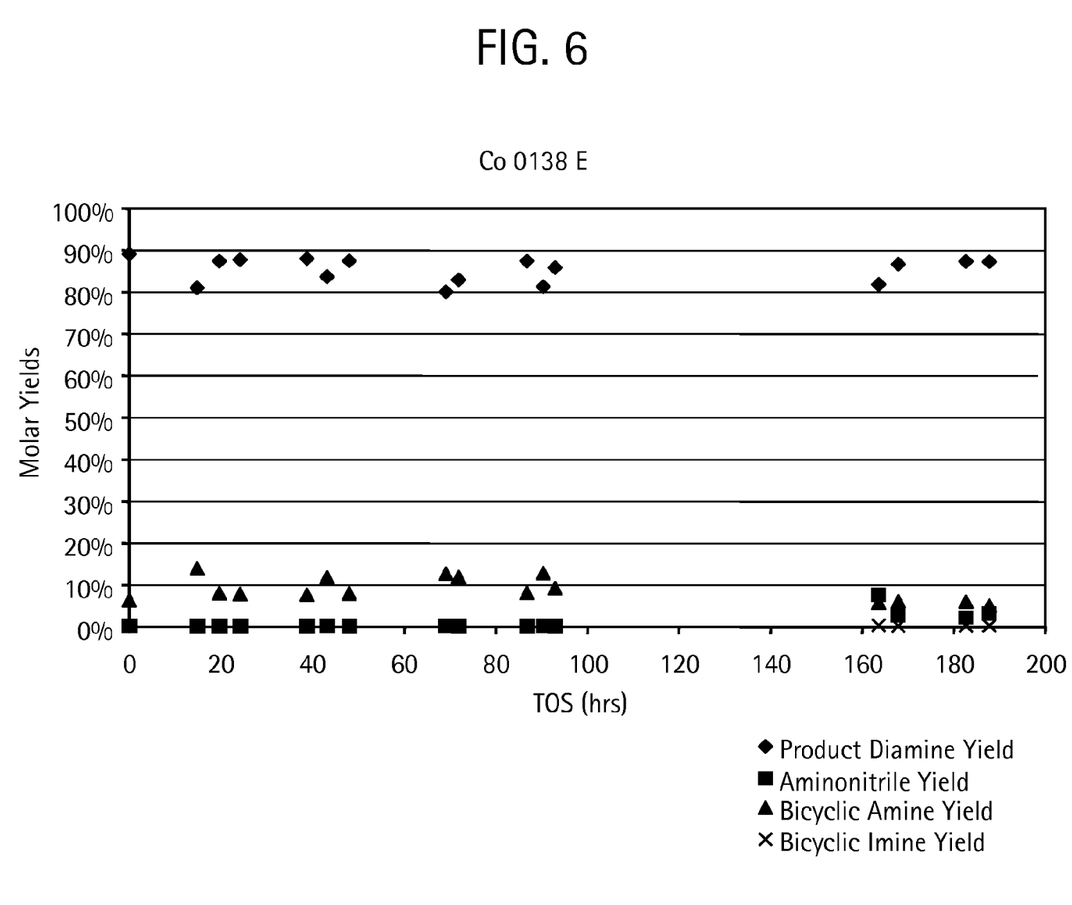
FIG. 6 is a graph illustrating the relationship between time on stream and molar yields of Inventive Example 4.

A reactor tube was loaded with 4.28 g Co-0138E catalyst provided by BASF, diluted with 100 grit (150 μm) SiC fines. The organic feed for this reactor was crude cycloaliphatic cyanoaldehydes (CCA) comprising approximately 85 to 90 percent by weight of cyanoaldehyde diluted to 25 weight percent with tetrahydrofuran (THF). The catalyst was treated with flowing hydrogen at 200° C. overnight prior to startup. After reducing the reactor temperature to <80° C. under continued hydrogen flow, an excess flow of ammonia (at least 3-5 times desired set point) was initiated. The temperature and pressure were then set to the desired set points of 100° C. and 1000 psig. After at least one hour, the ammonia was decreased to the desired set point of 0.11 mL/min, and the organic was started at 0.11 mL/min with a hydrogen to CCA molar ratio of 7. Samples were periodically collected from the reactor and analyzed by gas chromatography. Samples collected between 0 and 190 hours on stream showed 80-87 percent molar yield of diamines (1,3- and 1,4-bis(aminomethyl)cyclohexanes), with 0-7 percent molar yield of aminonitrile and 6-13 percent molar yield of bicyclic amine(3-azabicyclo[3.3.1]nonane). Catalyst performance is shown in FIG. 6.

Inventive Example 5

Figure 7:
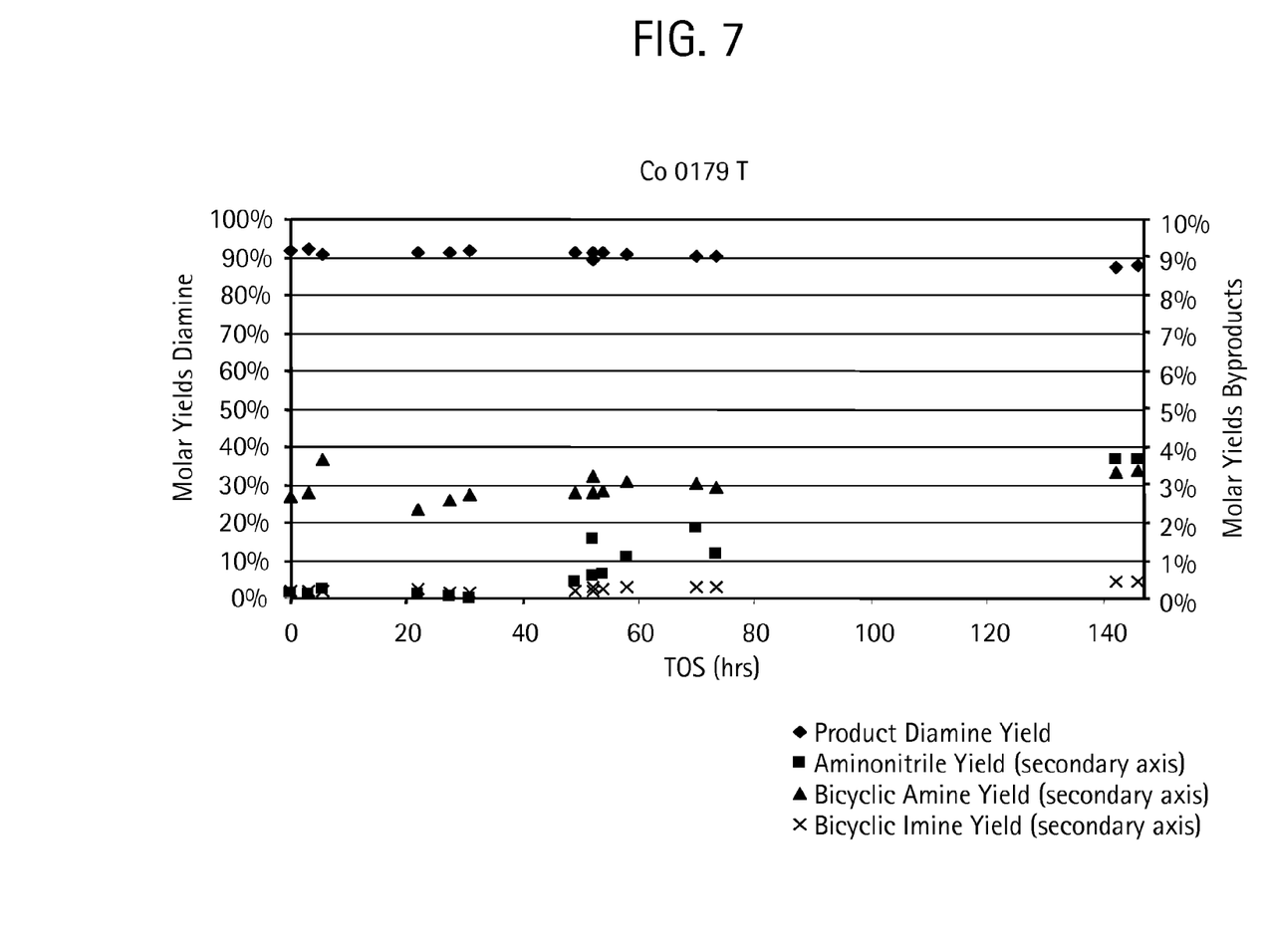
FIG. 7 is a graph illustrating the relationship between time on stream and molar yields of Inventive Example 5.

A reactor feed mixture was prepared by combining crude comprising approximately 85 to 90 percent by weight of cyanoaldehyde cyanoaldehyde with 20 wt % tert-butanol (t-butanol). The mixture was passed through a bed of sodium carbonate. A reactor tube was loaded with 6.5 g BASF catalyst Co-0179T, lot DM00042, diluted with 100 grit SiC fines. The catalyst was treated with flowing hydrogen at 233° C. overnight prior to startup. After reducing the reactor temperature to <80° C. under continued hydrogen flow, an excess flow of ammonia (at least 3-5 times desired set point) was initiated. The temperature and pressure were then set to the desired set points of 100° C. and 2000 psig. After at least one hour, the ammonia rate was decreased to the desired set point of 0.22 mL/min with an organic feed rate of 0.07 mL/min, a weight hourly space velocity (WHSV, based on combined organic and ammonia mass feed rates) of 2.8 $hr^{-1}$ with a hydrogen to CCA molar ratio of 5. Samples collected between 0 and 30 hours time on stream showed 91-92% molar yield of diamine (1,3- and 1,4-bis(aminomethyl)cyclohexanes), with 0-0.25% molar yield of aminonitrile and 2.3-3.6% molar yield of bicyclic amine(3-azabicyclo[3.3.1]nonane) (FIG. 7). After 50 hours of time on stream, the flow rates were increased for a combined WHSV of 4 $hr^{-1}$. Productivity at the higher rate was $1.23 \times 10^{-6}$ moles diamine/g-catalyst/s. Table 1 displays the cobalt leaching numbers in ppm (via ICP-MS). Again, higher pressures (2000 psig in this case) yielded lower cobalt in the diamine product.

The present invention may be embodied in other forms without departing from the spirit and the essential attributes thereof, and, accordingly, reference should be made to the appended claims, rather than to the foregoing specification, as indicating the scope of the invention.

TABLE 1

|  | Pressure (psig) | TOS (hours) | Cobalt (ppm) |
| --- | --- | --- | --- |
| Inventive Example 1 | 1070 | 810 | 25 |
| Inventive Example 1 | 1400 | 1244 | 6 |
| Inventive Example 1 | 1415 | 1350 | 5.1 |
| Inventive Example 5 | 2000 | 70-190 (composite) | 0.44 |

We claim:
1. A process for producing cycloaliphatic diamines comprising the steps of:
feeding one or more cycloaliphatic cyanoaldehydes selected from the group consisting of 3-cyanocyclohexane-1-carboxaldehyde, 4-cyanocyclohexane-1-carboxaldehyde, mixtures thereof, and combinations thereof, hydrogen, and ammonia into a reductive amination reactor system;
contacting said one or more cycloaliphatic cyanoaldehydes, hydrogen, and ammonia with each other in the presence of one or more heterogeneous metal based catalyst systems at a temperature in the range of from 80° C. to about 160° C. and a pressure in the range of from 700 to 3500 psig, wherein said catalyst system has a space velocity in the range of from 0.1 to 5.0 per hour, wherein space velocity is defined as the ratio of the mass of the mixture of one or more cycloaliphatic cyanoaldehydes to the mass of catalyst per hour;

thereby forming one or more cycloaliphatic diamines, wherein said one or more cycloaliphatic diamines are diamines selected from the group consisting of 1,3-bis(aminomethyl)cyclohexane, 1,4-bis(aminomethyl)cyclohexane, combinations thereof, and mixtures thereof.

2. The process according to claim 1, wherein said reductive amination reactor system comprises one or more continuous reactors in series, in parallel, or combinations thereof.

3. The process according to claim 1, wherein said one or more heterogeneous metal based catalyst systems comprises a metal selected from the group consisting of Co, Ni, Ru, Fe, Cu, Re, Pd, oxides thereof, mixtures thereof, and combinations thereof.

4. The process according to claim 1, wherein said one or more heterogeneous metal based catalyst systems is a bulk metal catalyst system, sponge-metal catalyst system, supported metal catalyst system, mixtures thereof, or combinations thereof.

5. The process according to claim 1, wherein said one or more heterogeneous metal based catalyst systems comprises a bulk Co based catalyst system.

6. The process according to claim 1, wherein said one or more heterogeneous metal based catalyst systems further comprises one or more promoters or one or more binding agents.

7. The process according to claim 6, wherein said one or more promoters are selected from the group consisting of alkali metals and alkaline earth metals.

8. The process according to claim 6, wherein said one or more binding agents comprise silicon oxide, aluminum oxide, titanium oxide, zirconium oxide, mixtures thereof, or combinations thereof.

9. The process according to claim 1, wherein the catalyst lifetime facilitates a weight ratio of said one or more cycloaliphatic diamines to said one or more heterogeneous metal based catalyst systems that is greater than 300.

10. A method of improving the production yield of cycloaliphatic diamines comprising the steps of: contacting one or more cycloaliphatic cyanoaldehydes selected from the group consisting of 1,3-cyanocyclohexane carboxaldehyde, 1,4-cyanocyclohexane carboxaldehyde, mixtures thereof, and combinations thereof, hydrogen, and ammonia with each other in the presence of one or more heterogeneous metal based catalyst systems at a temperature in the range of from 80° C. to about 160° C. and a pressure in the range of from 1400 to 2500 psig, wherein said catalyst system has a space velocity in the range of from 0.1 to 5.0 per hour, wherein space velocity is defined as the ratio of the mass of the mixture of one or more cycloaliphatic cyanoaldehydes to the mass of catalyst per hour; thereby improving the product yield of one or more cycloaliphatic diamines, wherein said one or more cycloaliphatic diamines are diamines selected from the group consisting of 1,3-bis(aminomethyl)cyclohexane, 1,4-bis(aminomethyl)cyclohexane, combinations thereof, and mixtures thereof.

* * * * *